(12) United States Patent
Miller

(10) Patent No.: US 12,734,064 B2
(45) Date of Patent: Sep. 15, 2026

(54) CONTACTLESS CPAP DEVICE

(71) Applicant: Spencer Miller, Dallas, TX (US)

(72) Inventor: Spencer Miller, Dallas, TX (US)

( * ) Notice: Subject to any disclaimer, the term of this patent is extended or adjusted under 35 U.S.C. 154(b) by 1001 days.

(21) Appl. No.: 17/378,525

(22) Filed: Jul. 16, 2021

(65) Prior Publication Data

US 2023/0014838 A1 Jan. 19, 2023

(51) Int. Cl.

| | |
|---|---|
| ***A61F 5/56*** | (2006.01) |
| ***A61M 16/00*** | (2006.01) |
| ***A61M 16/06*** | (2006.01) |
| ***A61M 16/20*** | (2006.01) |

(52) U.S. Cl.

CPC ......... *A61F 5/566* (2013.01); *A61M 16/0003* (2014.02); *A61M 16/0666* (2013.01); *A61M 16/208* (2013.01); *A61M 2016/0027* (2013.01); *A61M 2016/003* (2013.01)

(58) Field of Classification Search

CPC ............... A61F 5/566; A61M 16/0003; A61M 16/0666; A61M 16/208; A61M 16/049; A61M 2210/0625; A61M 2210/0637

See application file for complete search history.

(56) References Cited

U.S. PATENT DOCUMENTS 2,521,084 A 9/1950 Oberto
3,730,179 A 5/1973 Williams
5,375,593 A * 12/1994 Press ................. A61M 16/0666 128/207.18
5,513,634 A * 5/1996 Jackson ............ A61M 16/0495 128/207.14
5,752,510 A 5/1998 Goldstein
6,209,542 B1 4/2001 Thornton
6,571,798 B1 6/2003 Thornton
8,020,276 B2 9/2011 Thornton
8,236,216 B2 8/2012 Thornton
8,261,745 B2 9/2012 Chandran et al.
9,517,317 B2 12/2016 McAuley et al.
9,802,021 B2 10/2017 Tebbutt et al.
10,010,266 B2 7/2018 Hestness et al.
11,065,410 B1 * 7/2021 Feld .................. A61M 16/0683
11,458,036 B2 * 10/2022 Waterman ............... A61F 5/566
2005/0011523 A1 * 1/2005 Aylsworth .......... A61M 16/024 128/207.18

(Continued)

FOREIGN PATENT DOCUMENTS

EP 3823566 B1 * 10/2023 ............. A61F 5/566
WO WO-2007084940 A1 * 7/2007 ............... A62B 9/06
WO WO-2018067563 A1 * 4/2018 ........ A61M 16/0493

*Primary Examiner* — Kendra D Carter
*Assistant Examiner* — Maap Ellabib
(74) *Attorney, Agent, or Firm* — Patent Capital Group

(57) ABSTRACT

An apparatus for pressurizing one or more airways of a user, including: a dental arch mold configured to receive a plurality of teeth, a port which may be at a front face of the dental arch mold, a first nasal pillow, a second nasal pillow, a multi-output air regulator, and a plurality of sensors. The multi-output air regulator and sensors allow the airway pressurization device to sense the pressures in as well as be in independent fluid communication with the port of the dental arch, the first nasal pillow, and the second nasal pillow, such that an equalization of pressures, or a determined pressure differential between each may be obtained.

21 Claims, 5 Drawing Sheets

(56) References Cited

U.S. PATENT DOCUMENTS

2006/0096600 A1* 5/2006 Witt .................. A61M 16/0488 128/859
2006/0231101 A1 10/2006 Cannon
2007/0240718 A1* 10/2007 Daly ..................... A61M 16/08 128/204.22
2007/0272249 A1 11/2007 Chandran et al.
2008/0216831 A1 9/2008 McGinnis et al.
2010/0311003 A1* 12/2010 Kozlov ................... A61F 5/566 128/848
2011/0005531 A1 1/2011 Manzo
2011/0168188 A1 7/2011 Moore et al.
2018/0036503 A1* 2/2018 Mohamed ......... A61M 16/0666
2019/0175388 A1* 6/2019 Urban ..................... A61F 5/566
2019/0240435 A1* 8/2019 Anderson ......... A61M 16/0816

* cited by examiner 400
402
404
406
408
410
412

CONTACTLESS CPAP DEVICE

FIELD OF THE INVENTION

The present invention relates to airway pressure devices, specifically to selectable airway pressure devices.

DESCRIPTION OF THE RELATED ART

Sleep apnea is a potentially serious sleep disorder in which breathing repeatedly stops and starts. Sometimes, sleep apnea is caused by the brain not sending the proper signals to the muscles controlling breathing; however, more commonly sleep apnea is caused by the throat muscles relaxing. Left untreated, sleep apnea may increase the risk of other health problems, such as high blood pressure, heart failure, diabetes, and stroke, among a multitude of other issues.

There are multiple surgical and non-surgical ways to assist someone suffering from sleep apnea, however most people choose the non-surgical route. Such usually involves the use of airway pressurization and respiration devices, namely continuous positive airway pressure (CPAP) devices, which use pressure to keep the airways open during sleep.

In the related. a, it has been known to use different airway pressurization and respiration devices to create and maintain unobstructed airways, as well as eliminating snoring and sleep apnea in order to facilitate improved breathing in a user. These airway pressurization and respiration devices are oftentimes difficult to affix to face or airways of the user, are highly uncomfortable to wear, and/or oftentimes fail to securely hold a tight seal. Accordingly, these devices oftentimes do not function or perform as well as intended, Some of these devices provide positive pressure to just the nostrils of the user, while others provide positive pressure to both the nostrils and the mouth. The difference, from the user perspective, is often about comfort, but in some cases one or the other is preferred for therapeutic purposes. Where positive pressure is provided to both nostrils and the mouth it does not matter if the user breathes through the nostrils or the mouth, the same benefit is achieved.

Some improvements have been made in the field. Examples of references related to the present invention are described below in their own words, and the supporting teachings of each reference are incorporated by reference herein:

U.S. Pat. No. 3,730,179A, issued to Williams, discloses an invention that is a combination resuscitating, aspirating, and gastric draining apparatus of unitary construction which includes a tubular body, a portion of which is adapted for insertion into the mouth. A resuscitating supply source is detachably engaged with the tubular body. Nasal pharyngeal catheter tubes extend transversely through the tubular body for insertion into the nostrils for gastric draining, An oropharyngeal catheter tube extends longitudinally through the tubular body, for insertion down the throat. An aspirating source is operatively engaged with the nasal pharyngeal and oropharyngeal tubes.

U.S. Pat. No. 5,752,510A, issued to Goldstein, discloses an apparatus for alleviating a variety of breathing disorders, having a moldable mouthpiece clamped between the upper and lower teeth of the user so that a bracket outwardly projects from between the lips of the user in cantilevered fashion. The mouthpiece maintains the lower jaw forward to alleviate snoring problems by maintaining the throat clear. A nasal air delivery device is supported on the bracket and includes a pair of breathable air conducting tubes which terminate immediately adjacent to the user's nostrils. A sealing device disposed between the bracket and the nose prevents breathable air leakage, and a chin support carried on the tubes cooperates with the mouthpiece to stabilize and retain the nasal air delivery device in position on the facial area of the user.

U.S. Patent No.: 8,887,725B2, issued to Hernandez et al., discloses a respiration assist mask having an input gas feed tube, a ventilation interface, a facial interface and nasal. inserts. The gas feed tube can connect to the ventilation interface and form a seal. The ventilation interface may be joined with the facial interface to form a seal between the ventilation interface and the facial interface, as well as between the facial interface and the face of a user. Additionally, nasal inserts may be inserted into a portion of the facial interface and form a seal between the inserts and the facial interface.

U.S. Patent Application Publication No.: 2010/0311003A1, by Kozlov, discloses an invention relating to oral appliances configured to maintain users upper airway unobstructed, facilitating improved breathing and elimination of snoring and obstructive sleep apnea. The invention covers mechanical and pneumatic means of maintaining users airway open. A smart container for appliances is also disclosed to be used in conjunction with any oral appliance as a system for wirelessly recording patient biofeedback, treatment compliance and live monitoring of the users medical condition.

The inventions heretofore known suffer from a number of disadvantages which include: necessitating the device to touch the face of the user, having weak or inefficient sealing, necessitating headgear, likely disengagement from user movement, inability to control air flow or pressure, uncomfortable to use or wear, overly heavy or bulky, not properly pressurizing the mouth and nasal cavities, difficult to travel with or carry, and hard to properly clean.

What is needed is an apparatus, system, or method that solves one or more of the problems described herein and/or one or more problems that may come to the attention of one skilled in the art upon becoming familiar with this specification.

SUMMARY OF THE INVENTION

The present invention has been developed in response to the present state of the art, and in particular, in response to the problems and needs in the art that have not yet been fully solved by currently available docking and mooring devices. Accordingly, the present invention has been developed to provide a satisfactory docking and mot ring device.

There may be an apparatus for pressurizing one or more airways of a user, which may include one or more of the following a dental arch mold configured which may receive a plurality of teeth of a user, the dental arch mold may have a port which may be at a front face of the dental arch mold and may extend through to an interior thereof, a first nasal pillow which may be configured to be received by a nostril of a user, a second nasal pillow which may be configured to be received by a nostril of a user, a multi-output air regulator which may be capable of producing a plurality of different outputs which may have air pressures or air flow rates which are different from one another, the air regulator may be in independent fluid communication with at least two of: the port of the dental arch, the first nasal pillow, and the second nasal pillow, where the arch may extend past the rear molars of the user, where the arch may reach to the back of the jaw of the user and may fully occlude the mouth of the user when worn, where the first and second aspirating member may fully occlude the nostril of the user, a plurality of sensors which may be selected from the group of sensors which may consist of, air pressure sensors and air flow meters wherein at least two of the plurality of sensors may be located in a different air flow path from each other, where the multi-output air regulator may be in communication with the plurality of air sensors and may dynamically adjust air flow or air pressure at its various outputs based on information from the plurality of sensors, where the opening and closing of the valve may be based off the pressure of gas to one or more of the tubes, where the flow of gas to each of the plurality of tubes may be controlled individually and simultaneously by the valve, where there may be a plurality of valves, each valve may control the flow of gas to an individual tube, and a face shield which may he attached to each of the arch, first aspirating member, and second aspirating member.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included n at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment, in other instances, additional features and advantages may be recognized in certain embodiments that may not be present in all embodiments of the invention.

These features and advantages of the present invention will become more fully apparent from the following description and appended claims or may be learned by the practice of the invention as set forth hereinafter.

BRIEF DESCRIPTION OF THE DRAWINGS

In order for the advantages of the invention to be readily understood, a more particular description of the invention briefly described above will be rendered by reference to specific embodiments that illustrated in the appended drawing(s), It is noted that the drawings of the invention are not to scale. The drawings are mere schematics representations, not intended to portray specific parameters of the invention. Understanding that these drawings) depict only typical embodiments of the invention and are not, therefore, to be considered to be limiting us scope, the invention will be described and explained with additional specificity and detail through the use of the accompanying drawing(s), in which.

DETAILED DESCRIPTION OF THE INVENTION

Figure 1:
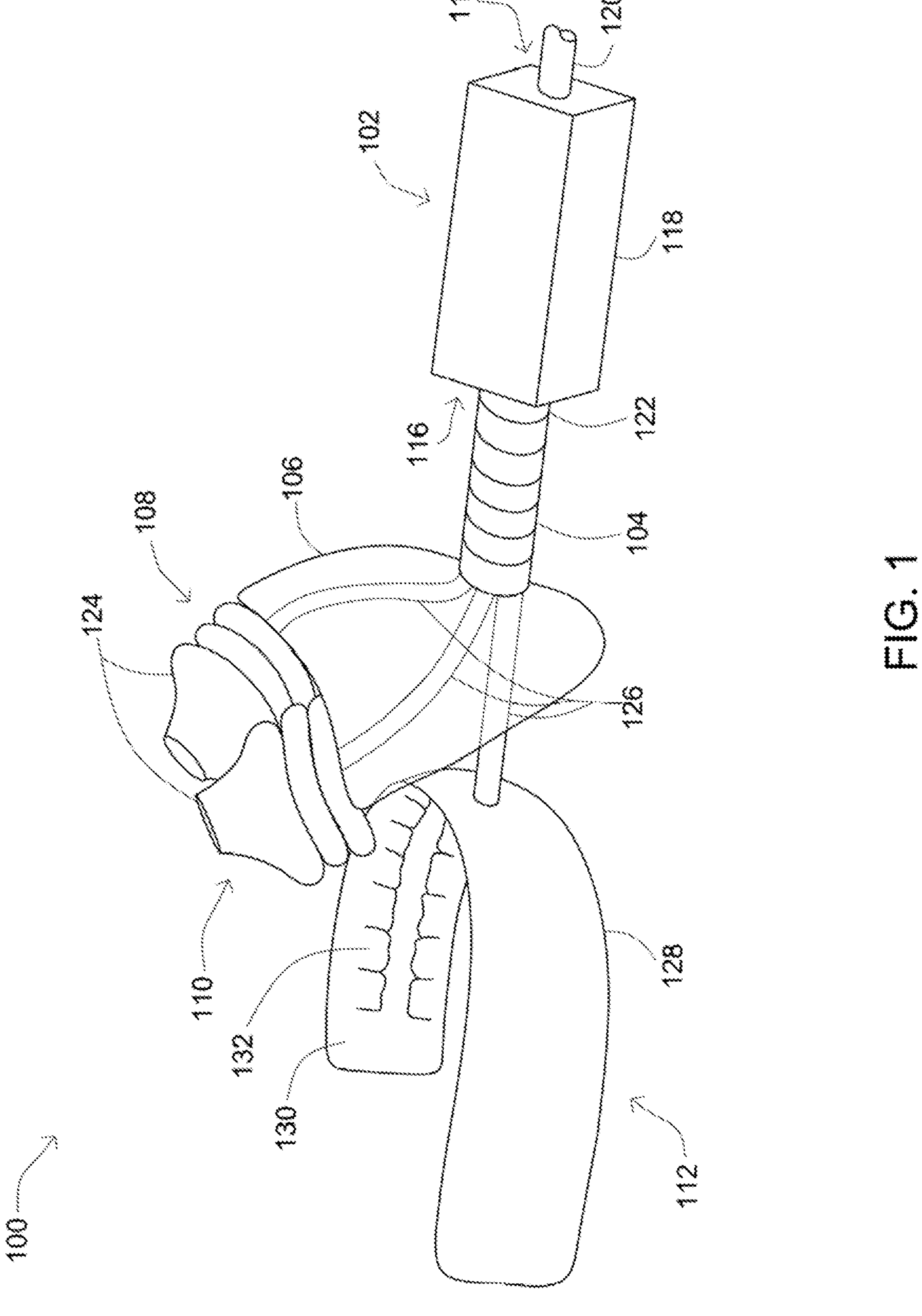
FIG. 1 is a top perspective view of a contactless CPAP device, according to one embodiment of the invention.

For the purposes of promoting an understanding of the principles of the invention, reference will now be made to the exemplary embodiments illustrated in the drawing(s), and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

Reference throughout this specification to an “embodiment,” an “example” or similar language means that a particular feature, structure, characteristic, or combinations thereof described in connection with the embodiment is included in at least one embodiment of the present invention. Thus, appearances of the phrases an “embodiment,” an “example,” and similar language throughout this specification may, but do not necessarily, all refer to the same embodiment, to different embodiments, or to one or more of the figures. Additionally, reference to the wording “embodiment,” “example” or the like, for two or features, elements, etc. does not mean that the features are necessarily related, dissimilar, the same, etc.

Each statement of an embodiment, or example, is to be considered independent of any other statement of an embodiment despite any use of similar or identical language characterizing each embodiment. Therefore, where one embodiment is identified as “another embodiment,” the identified embodiment is independent of any other embodiments characterized by the language “another embodiment.” The features, functions, and the like described herein are considered to be able to be combined in whole or in part one with another as the claims and/or art may direct, either directly or indirectly, implicitly or explicitly.

As used herein, “comprising,” “including,” “containing,” “is,” “are,” “characterized by,” and grammatical equivalents thereof are inclusive or open-ended terms that do not exclude additional unrecited elements or method steps. “Comprising” is to be interpreted as including the more restrictive terms “consisting of” and “consisting essentially of.”

FIG. 1 is a top perspective view of a contactless CPAP device, according to one embodiment of the invention, There is shown a CPAP device 100 including an air regulator 102, a conduit 104 connected to the air regulator 102, a face shield 106 connected to the conduit 104, a left nasal section 108 connected to the face shield 106, a right nasal section 110 connected to the face shield 106, and a mouth section 112 connected to the face shield 106. The illustrated CPAP device 100 includes separate airflow channels for each of the left nostril, right nostril, and mouth such that different positive pressure(s), air flow(s), and/or other airflow characteristics may be delivered independently through/to each separate airflow channel via the illustrated air regulator 102.

The illustrated air regulator 102 includes an input side 114, an output side 116, and a switching mechanism 118. The input side 114 is in fluid connection with the switching mechanism 118 and includes a single input port 120 wherethrough a gas (generally ambient air pumped by operation of an air pump of a CPAP system, not shown) may flow into air regulator 102. The input port 120 is sized such that a tube from a standard (TAP, APAP, BIPAP, or similar device easily connects to the input port 120, thus the illustrated system may be incorporated into existing CPAP solutions without requiring the user to purchase an entirely new system or discard their existing system, The input port may be a male or female connector, and may contain one or more of the following connectors: tapered, ribbed, barbed, quick-connect, twist lock, press-fit, universal and the like and combinations thereof to enable easy connecting and disconnecting of the air regulator to an air hose from an air flow device. In other embodiments, there may be more than one input port 120 or the input port 120 may contain multiple sections such that the inlet port 120 may connect to more than one CPAP, APAP, BIPAP, or similar device or may divert the air for the switching mechanism 118.

The output side 116 is in fluid communication with the switching mechanism 118 and includes a single output port 122 where through a gas may flow out from air regulator 102. The output port 122 may be sized and shaped such that the output port 122 may contain two or more air lines, as well as couple to a conduit 104 which may protect the air lines. The output port 122 may be a male or female connector, and may contain one or more of the following connectors: tapered, ribbed, barbed, quick-connect, twist lock, press-fit, universal and the like and combinations thereof to enable easy connecting and disconnecting of the air regulator to a section of conduit. In other embodiments, there may be more than one output port 122 or the output port 122 may contain multiple sections such that the output port 122 may connect directly to more than one air line or may divert the air to separate channels.

The switching mechanism 118 is in fluid communication with the input side 114 and output side 116. The switching mechanism 118 is designed to continuously sense or otherwise detect the pressure in the air lines exiting the output side 116 of the air regulator 102 and going to the left nasal section 108, right nasal section 110. and mouth section 112. The sensing mechanism is programmed to determine if the sensed pressure in each of the left nasal section 108, right nasal section 110, and mouth section 112 are where they are set to be, and if not, controls the airflow such that the pressure is increased or decreased from the input side 114 device to the respective section until it is where it is set to be. The switching mechanism may include one or more of the following devices, which control/manage airflow characteristics and which may be operated automatically and/or by computer control: valve, variable airflow restrictor, air pump, airflow diverter, actuator, pressure relief valve, air manifold, switches, and the like and combinations thereof.

In other embodiments, the switching mechanism 118 may be manually operated by the user such that the user must manipulate the switching mechanism 118 to control the pressure to each of the sections. Such may include multiple manual controls, such as but not limited to one for each airflow output channel. Once the pressure is at a comfortable or otherwise desirable level, the user may lock the switching mechanism 118 so that is does not change or simply leave it alone to maintain the settings at a desired level. This may be particularly advantageous where a user has a particular permanent condition, such as but not limited to a permanent airflow restriction in one nostril, that renders the existing CPAP systems ineffective, uncomfortable, or painful to use because the pressure or other airflow characteristict(s) are necessarily the same across all affected orifices.

The illustrated face shield 106 is connected to the conduit 104 and provides structure for the left nasal section 108, right nasal section 110, and mouth section 112 to connect to so that the con tactless CPAP device 100 has some rigidity to it and any air lines are able to be easily organized and run to each section and the air regulator 102 so that they do not kink or become tangled. In the illustrated embodiment, the face shield 106 does not touch the user's face, however in other embodiments it may be beneficial for the face shield 106 to contain hooks, straps, loops, and the like and combinations thereof to securely attach to the user's face.

The illustrated left nasal section 108 and right nasal section 110 are both rigidly connected to the face shield 106. The left and right nasal sections 108, 110, each include a nasal pillow 124 connected to a top end thereof and an air tube 126 which runs through the face shield 106 and conduit 104 and connects to the air regulator 102. The nasal pillow 124 is generally inserted into the nostril of the user and may consist of a frame section (strong structural) covered by a sealing section (soft sealing). The frame section is generally made of a strong yet lightweight material such as hard plastics or metals, while the sealing section sits on or over the frame section and is made of a flexible material such as a soft plastics, rubber foam or silicone. The frame section is designed to provide the structure for the sealing section to mount to, and the sealing section is designed to provide the flexibility to create a comfortable, yet airtight seal within the nasal passage of a wearer.

As the left and right nasal sections 108, 110, are designed to sit within the nasal passage of the wearer, the nasal pillows may be coated or impregnated with a chemical solution, oil, other coating to help them be resistant to mildew, mold, bacteria, odor and the like Although the left and right nasal sections 108, 110 are shown as being separate pieces, in other embodiments they may be connected, although the air tubes 126 running from each section are separate leading into the air regulator 102.

The illustrated mouth section 112 is rigidly connected to the face shield 106. Mouth section 112, includes a mouthguard 128 connected to an air tube 126 which runs through the face shield 106 and conduit 104 and connects to the air regulator 102. The mouthguard 128 may consist of a frame section covered by a sealing section. The frame section is generally made of a strong yet lightweight material such as hard plastics or metals, while the sealing section sits on or over the frame section and is made of a flexible material such as a soft plastics, rubber, foam, or silicone, The frame section is designed to provide the structure for the sealing section to mount to, and the sealing section is designed to provide the flexibility to create an airtight seal within the oral cavity of a wearer, The mouthguard 128 includes a cavity in the from thereof for the air tube 126 to connect and may be form fit to the specific user so that the mouthguard 128 seals around the teeth of the user. Additionally, the illustrated mouthguard 128 extends past the rear teeth (See protrusion 130 extending beyond the array of tooth imprints 132) of the user and is molded to the jaw of the user such that the mouthguard 128 fully forms a seal within the oral cavity, Further, as the mouth section 112 is designed to sit within the oral cavity of the wearer, the mouthguard and frame section may be coated or impregnated with a chemical solution, oil, other coating to help them be resistant to mildew, mold, bacteria, odor and the like.

Although the illustrated embodiment is shown with two nasal pillows 126 and a mouth guard, the left nasal section 108, right nasal section 110, and mouth section 112 in other embodiments may instead or in additionally include a full face and/or nasal/mouth mask, or cradle cushion depending on the user's needs and preferences. The contactless CPAP device 100 may be designed such that the left nasal section 108, right nasal. section 110, and mouth section 112 may be swapped out for different pieces easily depending on the situation.

The structural pieces of the contactless CPAP device 100 may be made of any material with a high strength-to-weight ratio, such as metals, hard plastics, wood, and the like and combinations thereof. These materials may be plated, coated or painted to assist in preventing exposure damage such as corrosion, chemical, or UV damage, as well as to provide antimicrobial properties.

In operation, the air regulator 102 is connected to an air flow device, such as a standard CPAP, APAP, BIPAP, or similar device. Once that connection is made, the air tubes from the left nasal section 108, right nasal section 110, and mouth section 112 are run through the face shield 106 and conduit 104 to the air regulator 102. The conduit 104 is then securely connected to the face shield 106 and air regulator 102. The user then inserts the left nasal section 108 and right nasal section 110 into the respective nasal cavities and the mouth section 112 into the oral cavity, and then sets the air regulator and air flow device and turns each on. Finally, the user seals the nasal and mouth sections such that the each form an airtight seal and are in a comfortable position. The above steps need not be necessarily done in the above order.

Advantageously, the contactless CPAP device 100 is a durable, comfortable., effective, and ready-to-use device that is able to direct the proper amount of airflow to the respective breathing cavities. The contactless CPAP device 100 is also designed to have a large amount of holding power while also minimizing the size of the unit and the amount of touching with the head oldie user. The device thereby both keeps the user comfortable and their airways properly pressured while also being significantly less likely to disengage.

Figure 2:
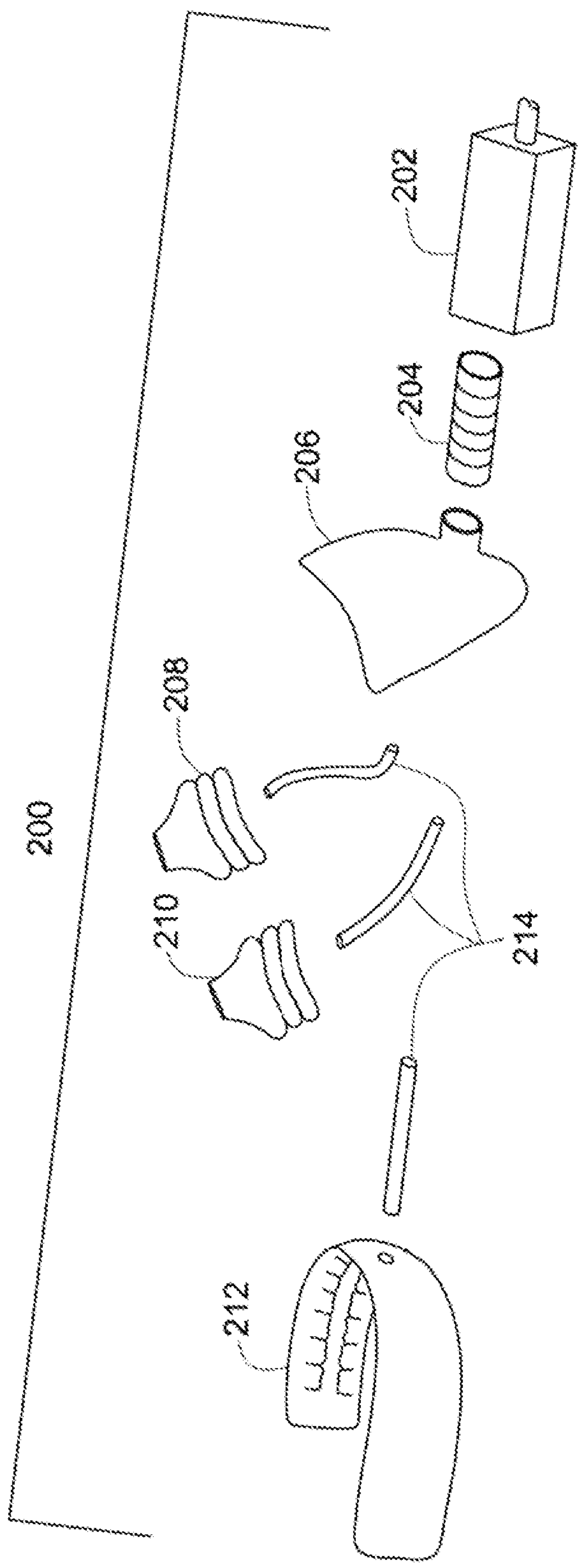
FIG. 2 is an exploded view of a contactless CPAP device, according to one embodiment of the invention.

FIG. 2 is an exploded view of a contactless CPAP device, according to one embodiment of the invention. There is shown a CPAP device 200 including an air regulator 202, a conduit 204 connected to the air, regulator 202, a face shield 206 connected to the conduit 204, a left nasal section 208 connected to the face shield 206, a right nasal section 210 connected to the face shield 206, and a mouth section 212 connected to the face shield 206.

As shown, the left nasal section 208, right nasal section 210, and mouth section 212 each have detachable air tubes 214 which connect the respective section through the face shield 206 and conduit 204 to the air regulator 202, This allows each individual section to be moved separately to comfortably rest in the respective air passage of the user, as well as allows the contactless CPAP device to be easily disassembled and cleaned when necessary, or for sections to be modified or replaced with sections that. better suit the individual user.

The illustrated embodiment shows the port of the face shield 206 to which the conduit 204 attaches to in order to keep the air tubes 214 safe from damage and tangle-free. The conduit 204 is shown to be flexible such that movements from the user do not detach any of the section from the user or the face shield 206 or air tithes 214 from the air regulator.

In some embodiments, the CPAP device 200 may be formed as a single unit or a few sections, such that most of or even all of the pieces shown are not detachable from one another. In this embodiment, the CPAP device 200 may use stiffer materials or supports, braces, etc. in order to provide rigidity to the system. The majority or entire CPAP device 200 may also be made out of a single printable or injection moldable plastic, however in some cases the individual pieces may be coated and/or with a more comfortable material or one that creates a better seal.

Figure 3:
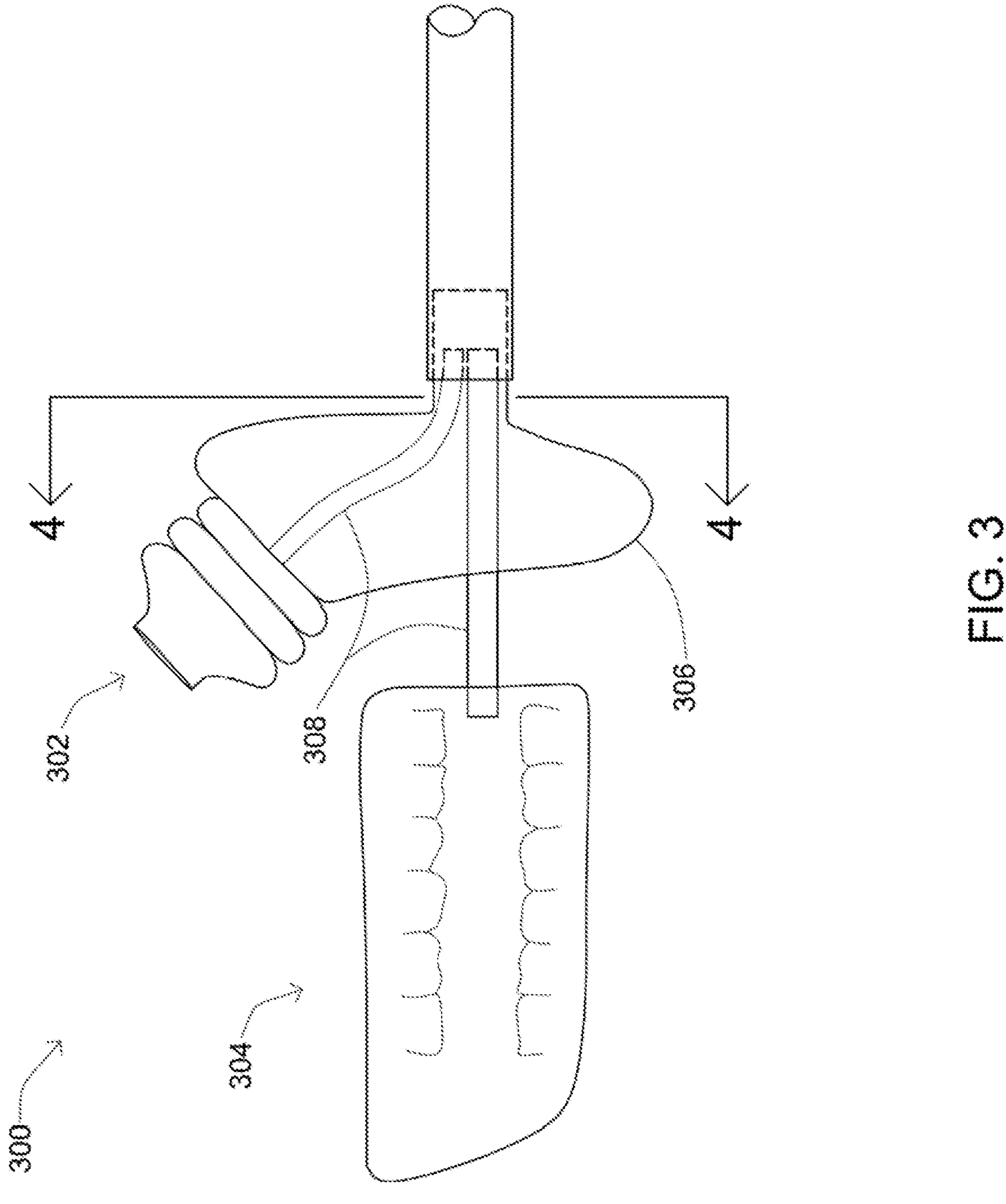
FIG. 3 is a side elevational view of a contactless CPAP device, according to one embodiment of the invention.

FIG. 3 is a side elevational view of a contactless CPAP device, according to one embodiment of the invention. The illustrated contactless CPAP device 300 is shown with the nasal section 302 and mouth section 304 rigidly attached to the face shield 306 (illustrated as a transparent plastic shield). Note that the cut for FIG. 4 is through the output side of the air regulator and the air lines 308 and faces towards the mouth section 304.

The illustrated mouth section 304 holds the jaw of a user slightly open as the teeth of the user are spaced apart to make room for airflow into the mouth. The spacing also supplies the room for the mouth tube 308 to be placed through and extend beyond an interior wall of the mouth section 304 so that airflow extends into the oral cavity. The protrusion of the mouth tube 308 into the interior of the mouth section 304 helps keep the mouth tube 308 in place, and in some embodiments, the mouth tube may be ribbed or have a bulbous section on the end to assist with keeping the mouth tube 308 from easily falling out.

Figure 4:
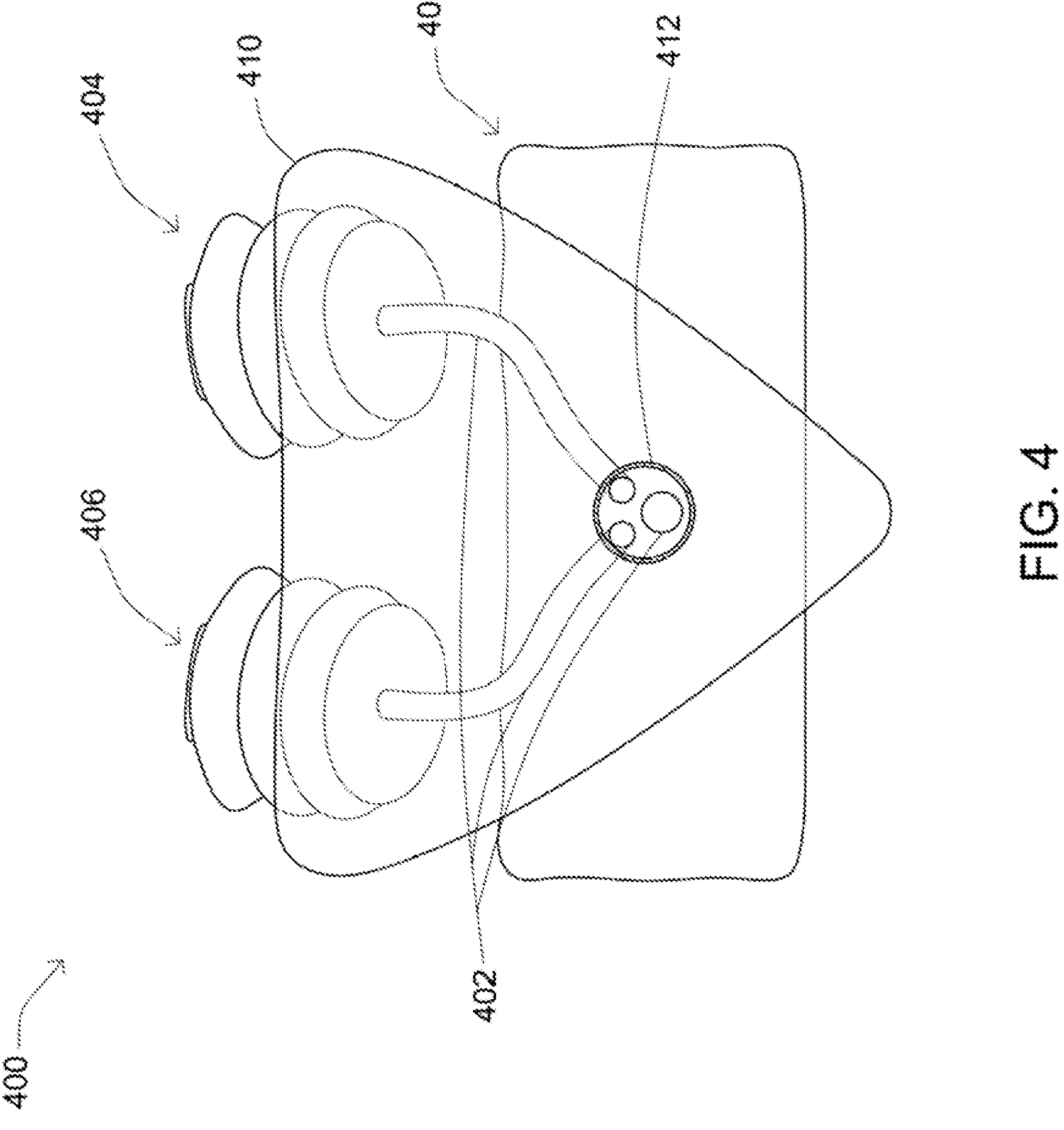
FIG. 4 is a cross-sectional view of a contactless CPAP device, according to one embodiment of the invention.

FIG. 4 is a cross-sectional view of a contactless CPAP device, according to one embodiment of the invention. The illustrated contactless CPAP device 400 is shown with the air tubes 402 connected to and extending from each of the left nasal section 404, right nasal section, 406, and mouth section 408, eventually arranged within and running through the face shield 410 (illustrated as a transparent plastic shield), all within a singular protective conduit 412 connected to and thereafter protruding from the face shield 410.

The illustrated contactless CPAP device 400 allows each of the left nasal section 404, right nasal section, 406 and mouth section 408 to be pressurized separately and at different levels from one another such that each airway passage receives the optimal amount of pressure and/or airflow. While there is shown spacing between the air tubes 402 within the protective conduit 412, there is generally no airflow within the conduit ## that is not also within at least one of the air tube 402 and any such airflow would only occur if there was a leak or disconnection of one of the air tubes 402. In such a situation, the user would experience airflow against their lips (even with only a slight leak), Which are very sensitive and thus the user could advantageously easily detect if the device was not fully or properly assembled.

Figure 5:
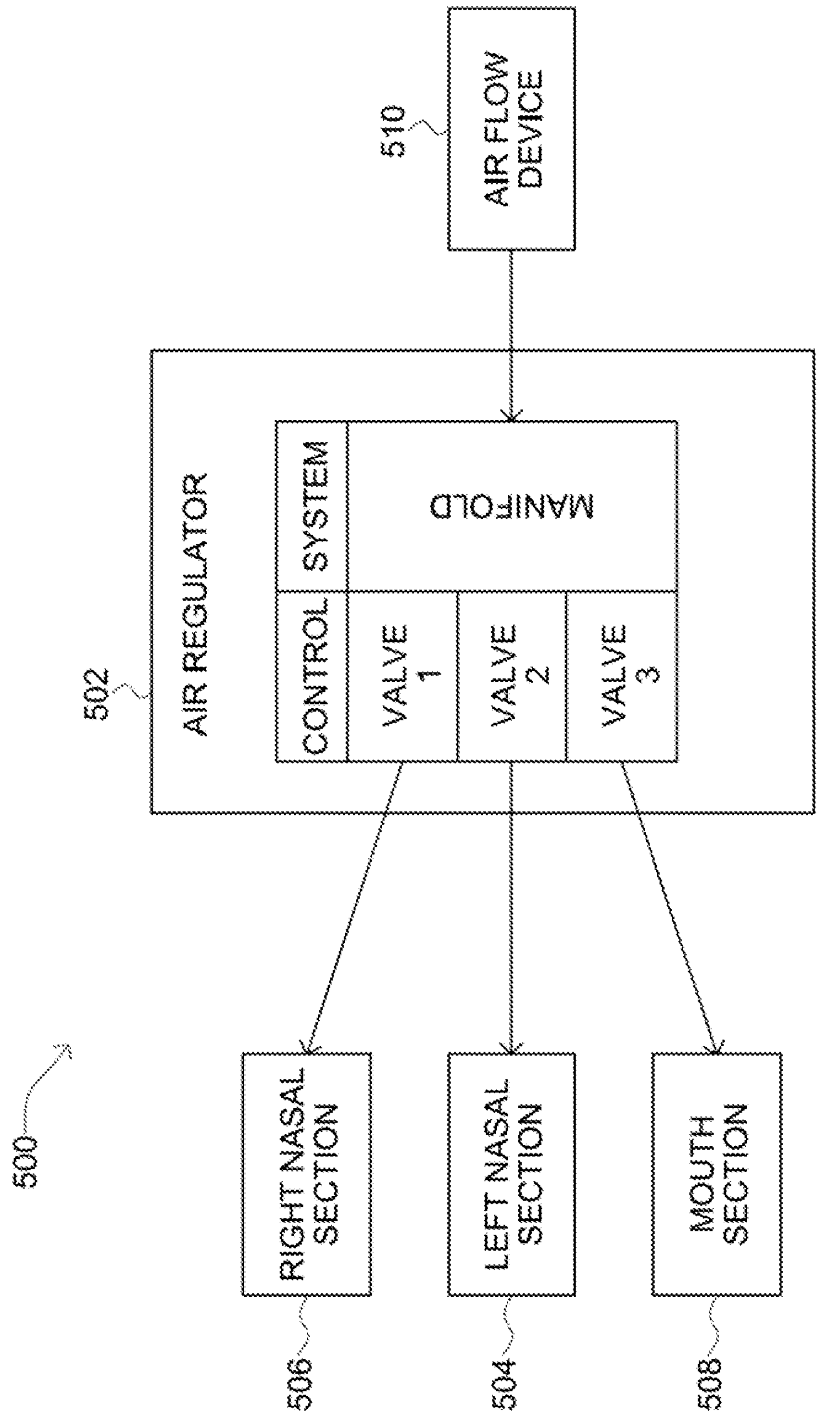
FIG. 5 is a module diagram of a contactless CPAP device, according to one embodiment of the invention.

FIG. 5 is a module diagram of a contactless CPAP device 500, according to one embodiment of the invention. The illustrated air regulator 502 is in communication with each of the left nasal section 504, the right nasal section 506, the mouth section 508, and the air flow device 510. The left nasal section 504, right nasal section 506, and mouth section 508 are each connected to the air regulator 502 via hollow tubes, however in some embodiments they may be more rigidly connected within or to form a unit. As with the lines to each cavity, the air flow device 510 is connected to the air regulator via one or more hollow tubes.

In operation, the, user may first desire to check each of the connections between each of the devices to ensure each are secure and airtight for operation. Once completed, the user may manually set the air regulator 502 and/or airflow device 510 and/or may select the setting or settings the user wishes the CPAP device 500 to follow once started.

Once device is set up and ready to operate, and any desired programming or settings are enabled, the left nasal section 504 right nasal section 506 are inserted into be user's left and right nostril, respectively, and mouth section 508 is inserted into the user's mouth, Each of the left nasal section 504, right nasal section 506 and mouth section 508 then may need to be manipulated such that each form a complete seal with the respective cavity to which they were inserted.

Once a complete seal for each has been achieved, the air flow device 510 is activated, and air begins to flow from the air flow device 510 to the air regulator 508. The air regulator 502 is generally initially fully open so that maximal air flow may be initially achieved through the left nasal section 504, right nasal section 506, and mouth section 508. However, in some embodiments, the air regulator may be initially shut so that tile airways do not receive any air initially or may be set in any desired state by the user, in those embodiments, the air regulator may be initially manually opened by the user, or may have a set initialization opening or be programmed to open by the user such that the left nasal section 504, right nasal section 506, and mouth section 508 do not initially take the full initial pressure wave.

In any of the above embodiments, air regulator 502 allows the control of the air to each of the left nasal section 504, right nasal section 506, and mouth section 508 to be individualized, such that air regulator 502 may be set to initialize or programmed by the user to open or close one or more of the sections differently from one another such that a sensitive airway, such as a deviated septum, does not take the rapid initial influx of air the same way a healthy nasal passage may be set to.

Once the initial airflow to each passage has been completed, the air regulator 502 senses the airflow to each of the left nasal section 504, right nasal section 506, and mouth section 508 through pressure sensors in each of the lines leading to the cavity and compares it to the settings it was desired to maintain. The air regulator 502 then adjusts the individual valves within itself to create more or less pressure in one car afore of the cavities. In other embodiments, the user may manually adjust the air regulator such that the device is comfortable to wear and providing the airflow the user desires.

The air regulator 502 then continues to run until shut off by the user, or after it has run for a predetermined amount of time. However, in some embodiments, the air regulator 502 may shut itself off if it senses a sudden and significant change in pressure to one of the left nasal section 504, right nasal section 506, and/or mouth section 508 to prevent aggravating an injury or to conserve energy if the device was removed however not shut off.

It is understood that the above-described embodiments are only illustrative of the application of the principles of the present invention. The present invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

For example, although the air regulator is designed to be able to control the flow of air to each cavity of the user, and accomplishes this by making modifications to itself such as closing valves or narrowing passageways, the air regulator may in some embodiments control the air flow device instead or in conjunction with itself. By slowing the rate of airflow from the air flow device it is connected to, the air regulator may have significantly more control over the pressure and air flow to the user such that a large pressure buildup does not occur right before the air regulator.

Additionally, although the figures illustrate a single CPAP device being fed by the air regulator, in other embodiments the air regulator may contain additional valves and input ports for multiple input devices such that a single air regulator may be used to control and regulate a plurality of units. An example is if it were to be used for people sharing a bed or a hospital situation wherein space to store and space to setup a system is limited.

It is also envisioned that the tubes of the system include stiffer bracing or are connected to supports such that they are significantly harder to kink, disengage, or cut open.

It is expected that there could be numerous variations of the design of this invention. An example is that the air regulator may instead of or in conjunction to sensing the pressure to each of the section, may sense and control the air flow to each of the sections.

Thus, while the present invention has been fully described above with particularity and detail in connection with what is presently deemed to be the most practical and preferred embodiment of the invention, it will be apparent to those of ordinary skill in the art that numerous modifications, including, but not limited to, variations in size, materials, shape, form, function and manner of operation, assembly and use may be made, without departing from the principles and concepts of the invention as set forth in the claims. Further, it is contemplated that an embodiment may be limited to consist of or to consist essentially of one or more of the features, functions, structures, methods described herein.

What is claimed is:

1. An apparatus for pressurizing one or more airways of a user, comprising:

a dental arch mold configured to receive a plurality of teeth of the user, configured to extend past the rear molars of the user to reach a back of a jaw of the user, and configured to occlude a mouth of the user when worn to form an airtight seal with an oral cavity of the user, the dental arch mold being configured to be form-fit to the user, molded to the jaw of the user, wherein the dental arch mold configured to hold teeth of the user spaced apart to make room for airflow into the mouth, and having a dental arch opening that extends at least through a front face of the dental arch mold to an interior side of the dental arch mold and extend beyond an interior wall of the dental arch mold so that airflow is configured to extend into the oral cavity of the user, wherein the dental arch opening defines a first airflow path to the oral cavity;

wherein the dental arch opening defines a first airflow path to the configured to be received by oral cavity of the user;

a first nasal pillow configured to be received by a first nostril of the user and to form an airtight seal with a first nasal passage of the user, wherein the first nasal pillow defines a second airflow path configured to be received by the first nasal passage; and a second nasal pillow configured to be received by a second nostril of the user and to form an airtight seal with a second nasal passage of the user, wherein the second nasal pillow defines a third airflow path configured to be received by the second nasal passage;

wherein the first airflow path, the second airflow path, and the third airflow path are configured to be pressurized independently from each other, and the apparatus is adapted to independently deliver different air pressures and/or air flow rates to each ach of the first airflow path, the second airflow path, and the third airflow path; a face shield attached to each of the dental arch mold, the first nasal pillow, and the second nasal pillow; a first air tube connected to the dental arch opening, a second air tube connected to the first nasal pillow, and a third air tube connected to the second nasal pillow, wherein the first air tube, the second air tube, and the third air tube run through the face shield; a protective conduit connected to the face shield, wherein the first air tube, the second air tube, and the third air tube run within the protective conduit; and a multi-output air regulator connected to the first air tube, the second air tube, and the third air tube, wherein the multi-output air regulator is capable of producing a plurality of different outputs having air pressures or air flow rates which are different from one another.

2. The apparatus of claim 1, wherein the first and second nasal pillows are configured to occlude a respective nostril of the user.

3. The apparatus of claim 1, further comprising a plurality of air pressure sensors and air flow meters wherein at least two of the plurality of air pressure sensors and air flow meters are located in a different air flow path from each other.

4. The apparatus of claim 3, wherein the multi-output air regulator is in independent fluid communication with at least two of the opening of the dental arch mold, the first nasal pillow, and the second nasal pillow, wherein the multi-output air regulator is in communication with the plurality of sensors and dynamically adjusts air flow or air pressure at the different outputs based on information from the plurality of sensors.

5. The apparatus of claim 1, further comprising: at least one valve, wherein opening and closing of the at least one valve is based on a pressure of gas to each of the first airflow path, the second airflow path, and the third airflow path.

6. The apparatus of claim 1, wherein a flow of gas to each of the first airflow path, the second airflow path, and the third airflow path is controlled individually by a valve.

7. The apparatus of claim 1, further comprising a plurality of valves, each valve controlling a flow of gas to an individual one of the first airflow path, the second airflow path, and the third airflow path.

8. The apparatus of claim 1, wherein the face shield is configured not to contact the user face.

9. The apparatus of claim 1, wherein each of the first nasal pillow and the second nasal pillow comprises a frame section covered by a sealing section, the frame section being made of a hard plastic or metal, and the sealing section being made of a flexible material, wherein the frame section is configured to provide structure for the sealing section to mount to, and the sealing section is configured to provide flexibility to create an airtight seal within a nasal passage of the user.

10. An apparatus for pressurizing one or more airways of a user, comprising: a dental arch mold configured to receive a plurality of teeth of the user, configured to extend past the rear molars of the user to reach a back of a jaw of the user, and configured to occlude a mouth of the user when worn to form an airtight seal with an oral cavity of the user, the dental arch mold being configured to be form-fit to the user, molded to the jaw of the user, wherein the dental arch mold configured to hold teeth of the user spaced apart to make room for airflow into the mouth, and having a dental arch mold port that extends at least through a front face of the dental arch mold to an interior side of the dental arch mold and extends beyond an interior wall of the dental arch mold so that airflow is configured to extend into the oral cavity of the user, wherein the dental arch mold port defines a first airflow path configured to be received by the oral cavity of the user;

a first nasal pillow configured to be received by a first nostril of the user and to form an airtight seal with a first nasal passage of the user, the first nasal pillow having a first nasal pillow port, wherein the first nasal port defines a second airflow path configured to be received by the first nasal passage;

a second nasal pillow configured to be received by a second nostril of user and to form an airtight seal with a second nasal passage of the user, the second nasal pillow having a second nasal pillow port, wherein the second nasal port defines a third airflow path configured to be received by the second nasal passage; and wherein at least two of the dental arch mold port, the first nasal pillow port, and the second nasal pillow port are connected to an individual one of the first air tube, the second air tube, and the third air tube and configured to be pressurized independently from each other;

a face shield attached to each of the dental arch mold, the first nasal pillow, and the second nasal pillow;

a first air tube connected to the dental arch mold port, a second air tube connected to the first nasal pillow port, and a third air tube connected to the second nasal pillow port, wherein the first air tube, the second air tube, and the third air tube run through the face shield;

a protective conduit connected to the face shield, wherein the first air tube, the second air tube, and the third air tube run within the protective conduit; and a multi-output air regulator connected to the first air tube, the second air tube, and the third air tube.

11. The apparatus of claim 10, wherein the first and second nasal pillow are configured to occlude a respective nostril of the user.

12. The apparatus of claim 11, further comprising a plurality of air pressure sensors and air flow meters wherein at least two of the plurality of air pressure sensors and air flow meters are located in a different air flow path from each other.

13. The apparatus of claim 12, wherein the multi-output air regulator capable of producing a plurality of different outputs having air pressures or air flow rates that are different from one another, the multi-output air regulator is in independent fluid communication with at least two of the first airflow path, second airflow path, and third airflow path, wherein the multi-output air regulator is in communication with the plurality of air pressure sensors and air flow meters and dynamically adjusts air flow or air pressure at the different outputs based on information from the plurality of air pressure sensors and air flow meters.

14. The apparatus of claim 13, further comprising: at least one valve, wherein opening and closing of the at least one valve is based on a pressure of gas of each of the first air tube, the second air tube, and the third air tube.

15. The apparatus of claim 14, wherein a flow of gas to each of the first air tube, the second air tube, and the third air tube is controlled individually by the valve.

16. The apparatus of claim 15, further comprising a plurality of valves, each valve controlling a flow of gas of an individual one of the first air tube, the second air tube, and the third air tube.

17. The apparatus of claim 16, wherein the face shield is configured not to contact the user face.

18. The apparatus of claim 16, wherein the protective conduit is further attached the multi-output air regulator.

19. The apparatus of claim 10, wherein the apparatus is adapted to independently deliver different air pressures and/or air flow rates to each of the first airflow path, the second airflow path, and the third airflow path.

20. The apparatus of claim 10, wherein the multi-output air regulator is configured to shut off upon sensing a sudden and significant change in pressure to one of the first airflow path, the second airflow path, or the third airflow path.

21. An apparatus for pressurizing one or more airways of a user, comprising:

a dental arch mold configured to receive a plurality of teeth of a user, configured to extend past the rear molars of the user to reach a back of a jaw of the user, and configured to occlude a mouth of the user when worn to form an airtight seal within an oral cavity of the user, wherein the dental arch mold configured to hold teeth of the user spaced apart to make room for airflow into the mouth, the dental arch mold having a dental arch opening that extends at least through a front face of the dental arch mold to an interior side of the dental arch mold and extends beyond an interior wall of the dental arch mold so that airflow is configured to extend into the oral cavity of the user, wherein the dental arch opening defines a first airflow path configured to be received by the oral cavity of the user;

a first nasal pillow configured to be received by and occluding a first nostril of the user wherein the first nasal pillow defines a second airflow path configured to be received by the first nostril;

a second nasal pillow configured to be received by and occluding a second nostril of the user, wherein the second nasal pillow defines a third airflow path configured to be received by the second nostril;

a plurality of air pressure sensors and air flow meters, wherein at least two of the air pressure sensors and air flow meters are located in a different air flow path from each other;

and a multi-output air regulator in communication with the plurality of air pressure sensors and air flow meters and capable of producing a plurality of different outputs having air pressures or air flow rates which are different from one another, wherein the first airflow path, the second airflow path, and the third airflow path are configured to be pressurized independently from each other; a face shield attached to each of the dental arch mold, the first nasal pillow, and the second nasal pillow; a first air tube connected to the dental arch opening, a second air tube connected to the first nasal pillow, and a third air tube connected to the second nasal pillow, wherein the first air tube, the second air tube, and the third air tube run through the face shield; and a protective conduit connected to the face shield, wherein the first air tube, the second air tube, and the third air tube run within the protective conduit.

* * * * *